(12) United States Patent
Palero et al.

(10) Patent No.: US 11,547,462 B2
(45) Date of Patent: Jan. 10, 2023

(54) RADIO FREQUENCY SKIN TREATMENT
(71) Applicant: KONINKLIJKE PHILIPS N.V., Eindhoven (NL)
(72) Inventors: Jonathan Alambra Palero, Eindhoven (NL); Marco Baragona, Eindhoven (NL); Martin Jurna, Eindhoven (NL); Margaret Ruth Horton, Eindhoven (NL); Babu Varghese, Eindhoven (NL)
(73) Assignee: KONINKLIJKE PHILIPS N.V., Eindhoven (NL)
( * ) Notice: Subject to any disclaimer, the term of this patent is extended or adjusted under 35 U.S.C. 154(b) by 950 days.
(21) Appl. No.: 15/529,659
(22) PCT Filed: Nov. 26, 2015
(86) PCT No.: PCT/EP2015/077709
§ 371 (c)(1),
(2) Date: May 25, 2017
(87) PCT Pub. No.: WO2016/087289
PCT Pub. Date: Jun. 9, 2016
(65) Prior Publication Data
US 2017/0319262 A1    Nov. 9, 2017
(30) Foreign Application Priority Data
Dec. 3, 2014    (EP) ..................................... 14196122
(51) Int. Cl.
*A61B 18/04* (2006.01)
*A61B 18/14* (2006.01)
*A61N 1/40* (2006.01)
*A61B 18/00* (2006.01)
*A61B 18/12* (2006.01)
(Continued)
(52) U.S. Cl.
CPC .............. *A61B 18/14* (2013.01); *A61N 1/403* (2013.01); *A61B 2018/0016* (2013.01);
(Continued)

(58) Field of Classification Search
CPC .............. A61B 18/14; A61B 2018/167; A61B 2018/128; A61B 2018/0016;
(Continued)

(56) References Cited

U.S. PATENT DOCUMENTS 6,379,350 B1 * 4/2002 Sharkey ............. A61B 18/1402
606/41
6,413,255 B1    7/2002 Stern
(Continued)

FOREIGN PATENT DOCUMENTS

WO        0053113 A1    9/2000
WO    2011092464 A1    8/2011
(Continued)

*Primary Examiner* — Kaitlyn E Smith
*Assistant Examiner* — Yasamin Ekrami

(57) ABSTRACT

A device for radio frequency (RF) skin treatment of skin of a user is provided. The device comprises an active electrode and a return electrode. The device further comprises an RF generator arranged to supply RF energy to the user's skin via the active electrode and the return electrode. The return electrode has a planar skin contact surface extending in a main plane. The active electrode has a skin contact surface with a maximum dimension in a range from 100 μm to 500 μm, and a surface area of the planar skin contact surface of the return electrode is at least 5 times larger than a surface area of the skin contact surface of the active electrode. The skin contact surface of the active electrode is arranged in a position at a distance from the main plane, seen in a direction perpendicular to the main plane. The device may be advantageously used, for example, to control the dimensions and shape of a thermal lesion in the user's skin generated by the RF energy.

18 Claims, 8 Drawing Sheets

(51) Int. Cl.
    *A61N 1/32* (2006.01)
    *A61B 18/16* (2006.01)
(52) U.S. Cl.
    CPC ............... *A61B 2018/0047* (2013.01); *A61B 2018/00577* (2013.01); *A61B 2018/00589* (2013.01); *A61B 2018/00601* (2013.01); *A61B 2018/00738* (2013.01); *A61B 2018/00922* (2013.01); *A61B 2018/128* (2013.01); *A61B 2018/142* (2013.01); *A61B 2018/1467* (2013.01); *A61B 2018/1475* (2013.01); *A61B 2018/167* (2013.01); *A61N 1/328* (2013.01)
(58) Field of Classification Search
    CPC .. A61B 2018/1475; A61B 2018/00601; A61B 2018/00589; A61B 2018/00577; A61B 2018/1467; A61B 2018/142; A61B 2018/00922; A61B 2018/00738; A61B 2018/0047; A61B 18/12; A61N 1/403; A61N 1/328
    See application file for complete search history.

(56) References Cited

U.S. PATENT DOCUMENTS

| | | | |
|---|---|---|---|
| 8,221,404 B2 | 7/2012 | Truckai | |
| 8,500,731 B2 | 8/2013 | Byrd | |
| 2002/0133149 A1* | 9/2002 | Bessette | A61B 18/14 606/41 |
| 2007/0112346 A1 | 5/2007 | Underwood | |
| 2007/0239075 A1* | 10/2007 | Rosenberg | A61N 1/0408 601/2 |
| 2008/0091182 A1 | 4/2008 | Mehta | |
| 2009/0093864 A1* | 4/2009 | Anderson | A61B 18/1477 607/88 |
| 2011/0218464 A1* | 9/2011 | Iger | A61B 18/14 601/2 |
| 2012/0150168 A1 | 6/2012 | Adanny | |
| 2013/0012891 A1 | 1/2013 | Gross | |
| 2013/0289679 A1* | 10/2013 | Eckhouse | A61N 1/06 607/102 |
| 2014/0207217 A1* | 7/2014 | Lischinsky | A61N 1/36014 607/102 |
| 2016/0213952 A1* | 7/2016 | Zovrin | A61N 7/00 |
| 2017/0202606 A1* | 7/2017 | Horton | A61B 18/1206 |

FOREIGN PATENT DOCUMENTS

| | | |
|---|---|---|
| WO | 2012023129 | 2/2012 |
| WO | 2014009875 A2 | 1/2014 |
| WO | 2014045216 A1 | 3/2014 |

* cited by examiner

RADIO FREQUENCY SKIN TREATMENT

This application is the U.S. National Phase application under 35 U.S.C. § 371 of International Application No. PCT/EP2015/077709, filed on Nov. 26, 2015, which claims the benefit of International Application No. 14196122.7 filed on Dec. 3, 2014. These applications are hereby incorporated by reference herein.

FIELD OF THE INVENTION

The invention relates to a device for radio frequency (RF) skin treatment of skin of a user.

BACKGROUND OF THE INVENTION

There are a number of skin treatment techniques in which thermal energy is delivered to the surface of the skin and underlying skin tissue to initiate a wound healing response. Thermal energy may be delivered to the skin by radio frequency (RF) energy, which is a form of electromagnetic energy. Skin treatment may be implemented by the creation of fractional non-ablative lesions using bipolar electrodes energized with RF energy. Creating fractional non-ablative lesions in skin tissue may improve the regeneration process of the skin tissue, wherein non-damaged skin tissue surrounding the lesions plays an important role in facilitating fast healing of the lesions. In RF-based skin treatment, a lesion may be created by RF-based thermolysis in a region of the users' skin that has received sufficient thermal dosage to thermally damage the skin, e.g. by inducing cell necrosis. Thermolysis or thermal decomposition is a chemical decomposition caused by heat. To achieve a safe and effective treatment by means of such application of RF energy, two important issues should be taken into account, i.e. preventing unwanted thermal damage of both target tissue and non-target tissue, and controlling the profile, i.e. the dimensions and shape of the thermal lesions depending on the desired type of treatment, e.g. wrinkle reduction or skin pigmentation treatment.

In publication US2012/0150168, an apparatus for RF skin treatment is described, wherein the apparatus includes an applicator with a tip that is populated by a plurality of voltage applying elements protruding from the tip surface and organized in one common cluster, and by a cluster of electrodes bounding the voltage applying elements and having an area larger than the voltage applying elements have. The apparatus applies voltage to the voltage applying elements with a magnitude sufficient to cause a desired skin effect. A current limiter limits the RF induced current, thereby preventing skin damage. The apparatus continuously senses the impedance of skin segments being treated, and adjusts the RF energy to a low skin impedance and/or stops the supply of RF energy in the case of too low or too high a skin impedance.

A problem of the apparatus disclosed in US 2012/0150168 is that it is not able to sufficiently control the desired profile, i.e. the dimensions and shape of the thermal lesions generated in the user's skin.

WO 2011/092464 A1 discloses an electrosurgical system including an electrosurgical instrument and an electrosurgical generator. The instrument has a longitudinal axis and includes at least first, second and third electrodes. The electrodes are spaced from each other by one or more insulating members therebetween, the spacing between the first and third electrodes being greater than the spacing between the first and second electrodes. The generator includes a source of radio frequency energy capable of producing either a coagulating RF waveform or a cutting RF waveform and has first, second and third output connections connected to, respectively, the first, second and third electrodes of the instrument. The generator further includes a switching means and a controller. When a cutting RF waveform is selected, the controller controls the switching means to direct the cutting RF waveform between the first and second output connections and, hence, between the first and second electrodes. When a coagulating RF waveform is selected, the controller controls the switching means to direct the coagulating RF waveform between the first and third output connections and, hence, between the first and third electrodes. The first electrode is an active electrode with a surface area smaller than the surface area of either the second electrode and the third electrode, which both act as a return electrode. In an embodiment, the first active electrode is arranged at a distal tip of the instrument, the second return electrode is annular and surrounds the first active electrode on a distally directed surface portion of the instrument, and the third return electrode is arranged on the instrument in an axially set-back position relative to the second return electrode.

US 2013/0012891 A1 discloses an apparatus for iontophoretic administration of a drug to human skin. The apparatus comprises a mount having a zone which is adhesively adherable to the skin. The mount is deformable in two different shapes in response to a deforming force, wherein one of the shapes is an unconstrained shape. The deformation of the mount into the unconstrained shape is a sudden deformation, and by deformation of the mount into the unconstrained shape a treatment unit is moved into a position to apply treatment to the skin. The treatment unit comprises a reservoir for a negatively-charged drug molecule to be administered and a cathode connected to a power supply. An anode is arranged in another location on the skin-facing side of the mount and is also connected to the power supply.

SUMMARY OF THE INVENTION

An object of the present invention is to improve a device for RF skin treatment by enabling improved control of the desired profile of the thermal lesions generated in the user's skin.

According to the invention, this object is achieved by a device for RF skin treatment of skin of a user, the device comprising:

an active electrode having a skin contact surface with a maximum dimension in a range from 100 µm to 500 µm;

a return electrode having a planar skin contact surface, the planar skin contact surface of the return electrode extending in a main plane; and an RF generator arranged to supply, during use, RF energy to the skin via the active electrode and the return electrode; wherein a surface area of the planar skin contact surface of the return electrode is at least 5 times larger than a surface area of the skin contact surface of the active electrode; and wherein the skin contact surface of the active electrode is arranged or arrangable in a position at a distance from the main plane, seen in a direction perpendicular to the main plane.

The skin treatment device according to the invention may be used in a method for RF skin treatment of skin of a user, the method comprising the steps of:

placing the skin treatment device in pressure contact with the user's skin;

after placing the skin treatment device on the user's skin, supplying RF energy to the user's skin via the active electrode and the return electrode.

The invention relates to an RF skin treatment device wherein the skin contact surface of the active electrode has a maximum dimension in the range from 100 μm to 500 μm and wherein the surface area of the planar skin contact surface of the return electrode is at least 5 times larger than the surface area of the skin contact surface of the active electrode. This electrode configuration enables the creation of a local lesion immediately below the active electrode.

It is noted that the expression "maximum dimension" of the skin contact surface of the active electrode refers to a maximum distance present between two points on an outer circumference of the skin contact surface. Accordingly, the outer circumference can have any shape, such as a circular, square, triangular or rectangular shape. For example, in case of a circular shape of the outer circumference of the skin contact surface, said maximum dimension corresponds to the diameter of the outer circumference.

The invention involves an arrangement of the active electrode and the return electrode such that, after placement of the device in pressure contact with the user's skin, the skin contact surface of the active electrode is at a distance from the main plane defined by the planar skin contact surface of the return electrode. As a result, when sufficient pressure is exerted on the device, the active electrode and the return electrode make contact with the user's skin at two different skin surface levels, i.e. under local deformation of the skin surface. Herein, the term 'skin surface level' refers to the level of the skin underneath the electrodes.

The present invention is based on the insight that control of the RF delivery to the skin may be achieved by locally deforming the skin by means of the electrodes, for example by creating a protrusion or indentation in the skin by means of the electrodes, i.e. by means of a suitable geometry and arrangement of the RF bipolar electrode system comprising the active electrode and the return electrode. By locally deforming the skin by means of the electrodes according to the invention, the profile of the local lesion formed immediately below the active electrode can be adjusted to a substantial extent. The dispersion of the electric field lines in the skin extending from the active electrode to the return electrode determines the thermal dosage of the RF energy locally applied to the skin. A concentration of the electric field lines in the skin in the region immediately below the active electrode results in the creation of a local lesion below the active electrode. A variation of the distribution of the electric field lines will locally alter the density distribution of the electric field lines and, consequently, will alter the dimensions, i.e. the depth and width, of the lesion. A controlled local deformation of the skin near the active electrode therefore results in a controlled variation of the distribution of the electric field lines near the active electrode and, thereby, in control of the profile, i.e. the dimensions and shape of the lesions created in the user's skin.

The penetration depth of the RF energy, and thus the depth of the created thermal lesions, is dependent on the electrical conductance of the tissue, which is frequency-dependent, as well as on the exposure time of the RF energy. The lesion depth may be increased by exposing the tissue to an RF pulse with a duration longer than the thermal relaxation time of the skin tissue, thus allowing the generated heat to diffuse into deeper areas resulting in a bigger lesion, i.e. a lesion which is both deeper and wider. It is however undesirable to expose the skin to high temperatures for long periods of time due to an increased pain perception. By locally deforming the skin during the RF delivery, the invention provides a useful and robust device by means of which the lesion profile can be controlled independent of the RF frequency, RF pulse duration, and tissue impedance.

It is noted that a deformation of the skin may be created by the active electrode and/or by the return electrode or by other means, for example, by an outer surface of the device. It is also noted that the desired lesion profile may depend on the desired type of treatment. For the treatment of fine lines and wrinkles, relatively deep and narrow lesions are desired, because the efficacy of the treatment result depends on the depth of the denatured dermal collagen that will eventually regenerate and form the basis of renewed skin tissue, while minimizing the side effects. In the treatment of skin pigmentation, where an even skin tone is the desired benefit, the target tissue is within the epidermis and relatively shallow and wide lesions are desirable. Furthermore, wide and shallow lesions are desired for applications that aim to enhance the skin transdermal penetration of active substances. Thus, an RF skin treatment device that enables control of the lesion profile, i.e. the lesion depth and width, depending on the desired skin benefit will be advantageous.

In a preferred embodiment of the device according to the invention, the distance between the skin contact surface of the active electrode and the main plane is larger than 0.5 mm. When said distance is larger than 0.5 mm, a substantial adjustment of the lesion profile is achieved, which enables the use of the device for different treatments.

In a preferred embodiment of the device according to the invention, the skin contact surface of the active electrode has a circular circumference with a diameter in a range from 100 μm to 500 μm. A circular shape of the contact surface of the active electrode prevents the occurrence of local hot spots in the thermal lesion, which could result in unwanted high temperature peaks and local ablation of skin tissue.

In a preferred embodiment of the device according to the invention, the return electrode surrounds the active electrode. The arrangement of the return electrode relative to the active electrode according to this embodiment facilitates the desired deformation of the user's skin. This may advantageously further enhance the control of the deformation of the treatment region and the control of the profile of the lesions created therein. Preferably, the planar skin contact surface of the return electrode is annular, and the active electrode is arranged on a center line of the planar skin contact surface.

In an embodiment wherein the return electrode has an annular planar skin contact surface, the planar skin contact surface preferably has an inside diameter between 1 and 4 mm and a radial width between 1 and 5 mm. In this preferred embodiment the radial width is half the difference between the outside diameter and the inside diameter of the planar skin contact surface of the return electrode. In this embodiment, a relatively large planar skin contact surface of the return electrode compared to the skin contact surface of the active electrode provides an increased density of the RF electrical field lines in the skin tissue immediately below the active electrode and, thereby, advantageously increases the possible degree of adjustment of the profile of the lesion generated immediately below the return electrode.

In a preferred embodiment of the device according to the invention, an outer surface of the device comprises a protrusion, wherein the active electrode is arranged on top of the protrusion, and wherein the return electrode is arranged adjacent to the protrusion. In this embodiment, by placing the active electrode and the return electrode in contact with the skin, the skin is deformed prior to delivery of the RF energy. In particular, the protrusion forms an indentation into the skin surface, as a result of which the active electrode arranged on top of the protrusion will be positioned at a deeper skin surface level as compared to the return electrode. This position of the active electrode will particularly result in a relatively shallow and wide local lesion generated immediately below the active electrode, which is particularly effective for treatment of the epidermis.

Preferably, the protrusion is dome-shaped. This enhances the deformation of the user's skin to a desired shape, and the deformation of the skin is reproducible to a high degree, so that the adjustment and control of the deformation of the user's skin, based on the desired type and amount of treatment, are reliable. It is noted that the protrusion may have a hemispherical shape, or shapes other than a dome shape, e.g. a conical shape.

In a preferred embodiment of the device according to the invention, at least an outer surface of the protrusion is made of an electrically insulating material. In this manner, dispersion of the RF electric field outside the targeted treatment region in the user's skin immediately below the active electrode is limited. This may advantageously lead to a more efficient treatment and control of the lesion profile.

In a preferred embodiment of the device according to the invention, an outer surface of the device comprises an indentation, wherein the active electrode is arranged in the indentation, and wherein the return electrode is arranged adjacent to the indentation. In this embodiment, by placing the active electrode and the return electrode in contact with the skin, the skin is deformed prior to delivery of the RF energy. In particular, the indentation forms a protrusion or skin dome on the skin surface, as a result of which the active electrode arranged in the indentation will be positioned at a higher skin surface level as compared to the return electrode. This position of the active electrode will particularly result in a relatively narrow and deep local lesion generated immediately below the active electrode, which is particularly effective for treatment of the upper portion of the dermis layer. The active electrode may preferably be arranged in a deepest position in the indentation.

Preferably, the indentation is dome-shaped. This enhances the deformation of the user's skin to a desired shape, and the deformation of the skin is reproducible to a high degree, so that the adjustment and control of the deformation of the user's skin, based on the desired type and amount of treatment, are reliable. It is noted that the indentation may have a hemispherical shape, or a shape other than a dome shape, e.g. a conical shape.

In a preferred embodiment of the device according to the invention, at least an inner surface of the indentation is made of an electrically insulating material. In this manner, dispersion of the RF electric field outside the targeted treatment region in the user's skin immediately below the active electrode is limited. This may advantageously lead to a more efficient treatment and control of the lesion profile.

In a preferred embodiment of the device according to the invention, the active electrode is displaceable relative to the return electrode, and the device comprises adjusting means configured for adjusting the distance between the contact surface of the active electrode and the main plane. This embodiment, for example, enables the user to select or set a specific distance between the contact surface of the active electrode and the main plane, or said distance may, for example, be automatically set by the device in dependence on a user input relating to a desired treatment or relating to certain properties of the skin. Thus, this embodiment provides the user with a possibility to select or control the desired treatment, particularly also in dependence on certain properties of the skin, e.g. the mechanical stiffness of the skin.

In a preferred embodiment of the device according to the invention, the device comprises a skin-contact element which, in use, contacts the user's skin, wherein the skin-contact element comprises an opening having a main axis of extension, and wherein the active electrode is displaceably arranged in said opening and displaceable into a plurality of different positions along said main axis of extension. This may be advantageous in that it makes it possible for the user to choose a specific axially protruding position depending on the desired treatment. This may advantageously provide user-specific and treatment-specific user control of the device.

In a preferred embodiment of the device according to the invention, the device comprises a plurality of active electrodes, and the skin-contact element comprises a plurality of openings, each active electrode being displaceably arranged in a corresponding one of the openings. This embodiment enables the user to perform a quicker and more uniform skin treatment in a targeted region of the user's skin.

In a preferred embodiment of the device according to the invention, the device comprises a rotatable assembly and a plurality of active electrodes arranged in the rotatable assembly, the rotatable assembly comprising a cylindrical skin-contact element comprising a plurality of openings, wherein each active electrode is displaceably arranged in a corresponding one of the openings. In this embodiment, the rotatable assembly carrying the plurality of active electrodes can be rolled over the skin surface. This may advantageously facilitate the usage of the device by the user.

Preferably, the rotatable assembly comprises transmission means rotatably arranged inside the rotatable assembly and arranged to control the positions of the active electrodes in the corresponding openings. The transmission means enable a convenient setting of the positions of the active electrodes in the openings and, thereby, of the distance between the skin contact surface of each of the active electrodes and the main plane of the corresponding return electrode.

It will be appreciated by those skilled in the art that two or more of the above-mentioned embodiments, implementations, and/or aspects of the invention may be combined in any way deemed useful.

Modifications and variations of the method which correspond to the described modifications and variations of the device, can be carried out by a person skilled in the art on the basis of the present description.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

Figure 1A:
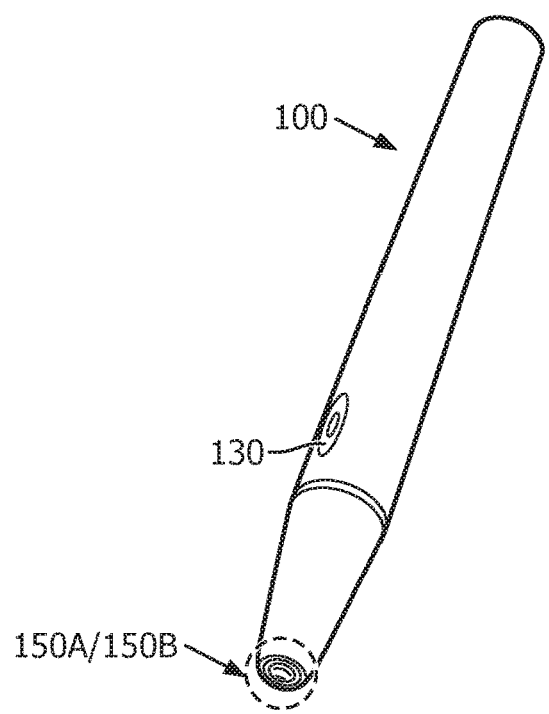
FIG. 1A shows a perspective view of a device for RF skin treatment according to an embodiment of the invention.
Figure 1B:
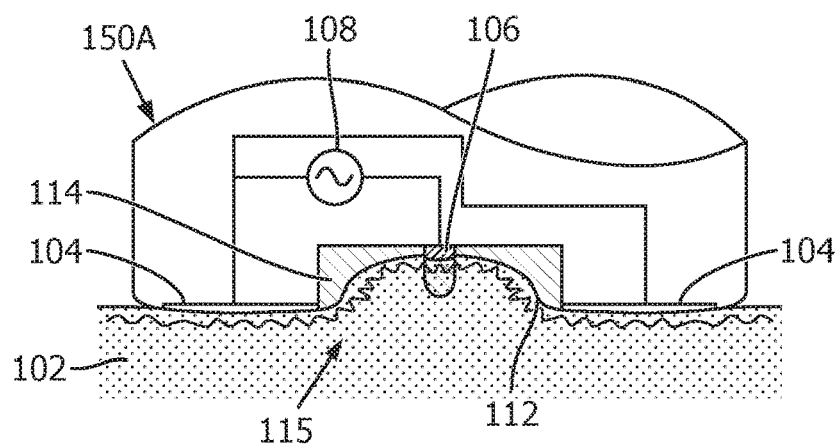
FIG. 1B shows a cross-sectional view of an applicator-skin interface of the device of FIG. 1A for deep treatment of the skin, which device is positioned on a user's skin.

FIG. 1A shows a perspective view of a device 100 for RF skin treatment according to an embodiment of the invention. The device 100 is a pen-like device 100 comprising a control interface button, e.g. a power button 130, and a skin-contact element which may be an applicator-skin interface 150A for deep treatment of the skin or an applicator-skin interface 150B for superficial treatment of the skin. FIG. 1B shows a cross-sectional view of the deep-treatment applicator-skin interface 150A positioned on a user's skin 102. The deep-treatment applicator skin-interface 150A comprises a microelectrode 106 acting as an active electrode and a return electrode 104 surrounding the microelectrode 106. A tip of the microelectrode 106 is arranged in an indentation 115 of the deep-treatment applicator-skin interface 150A such that, in use, the tip of the microelectrode 106 is in electrical contact with an upper region of a protruding skin region 112, while the return electrode 104 is in electrical contact with a flat undeformed portion of the surface of the skin 102. The indentation 115 in this example is a dome-shaped cavity made in an insulating element 114 surrounding the microelectrode 106, which indentation, in use, at least partially encloses the protruding skin region 112. At least an inner surface of the insulating element 114 is made from an electrically insulating material. It is noted that the protruding skin region 112 is formed by applying mechanical contact pressure on the skin 102 using the pen-like device 100.

Figure 1C:
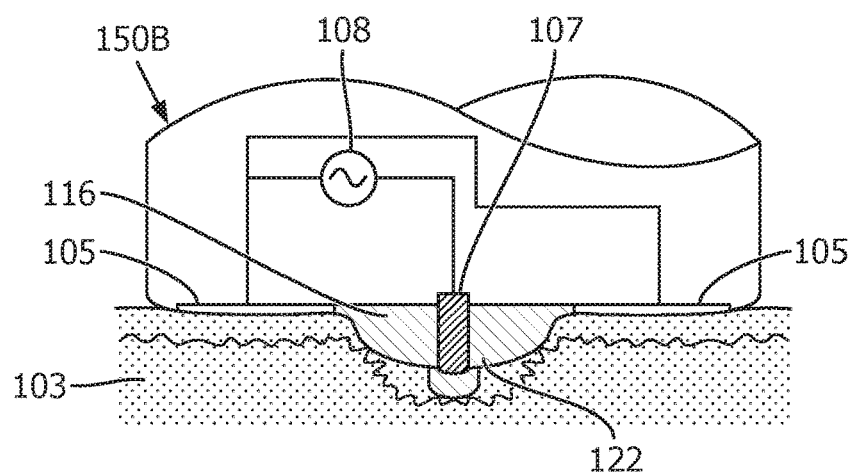
FIG. 1C shows a cross-sectional view of an applicator-skin interface of the device of FIG. 1A for superficial treatment of the skin, which device is positioned on a user's skin.

FIG. 1C shows a cross-sectional view of the applicator-skin interface 150B for superficial treatment of the skin, wherein the applicator is positioned on a user's skin 103. Said applicator-skin interface 150B for superficial treatment of the skin comprises a protrusion 116 which is, in this example, a dome-shaped tip that, in use, creates an indented skin region or skin indentation 122 formed by applying mechanical contact pressure on the skin 103 using the pen-like device 100. At least an outer surface of the protrusion 116 is made of an electrically insulating material. The applicator-skin interface 150B for superficial treatment of the skin further comprises a return electrode 105 and a microelectrode 107 acting as an active electrode. A tip of the microelectrode 107 is positioned on top of the protrusion 116 such that, in use, the tip of the microelectrode 107 is in electrical contact with an upper region of the indented skin region 122 while the return electrode 105 is in electrical contact with a flat undeformed portion of the surface of the skin 103.

It is noted that the indentation 115 or the protrusion 116 may have other shapes, e.g. a conical shape. It is also noted that the electrically insulating material may be any electrically non-conducting material, e.g. Teflon. The electrically insulating material may be a bio-compatible material.

The microelectrodes 106, 107 may have a skin contact surface with a circular outer circumference having a diameter between 100 μm and 500 μm. The surrounding return electrode 104, 105 may be a ring-shaped electrode with an inside diameter between e.g. 1 and 4 mm and with a radial width between e.g. 1 and 5 mm. The radial width is half the difference between the outside diameter and the inside diameter of the return electrode 104, 105. Other dimensions are possible.

It is noted that the pen-like device 100 further comprises an RF generator, herein also referred to as RF source, which is indicated by reference numeral 108 in FIG. 1B and 1C. The RF source 108 may have an RF frequency between e.g. 300 kHz and 25 MHz, and may have an RF voltage output between e.g. 10 and 150 root-mean-square (rms) Volts. Other frequencies and voltages are possible.

Figures 2A, 2B:
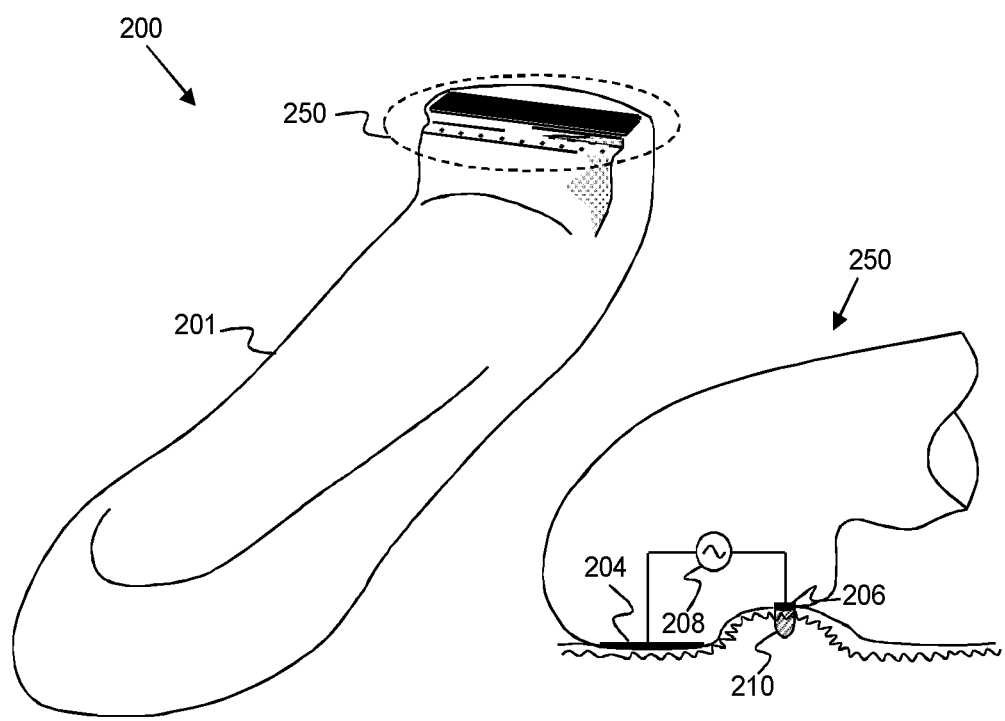
FIG. 2A shows a perspective view of a shaver-like device for RF skin treatment according to another embodiment of the invention.
FIG. 2B shows a cross-sectional view of an applicator-skin interface of the device of FIG. 2A positioned on a user's skin.

FIG. 2A shows a perspective view of a device 200 for RF skin treatment according to an embodiment of the invention. This device 200 comprises a shaver-like housing 201 and an applicator-skin interface 250. FIG. 2B shows a cross-sectional view of the applicator-skin interface 250 positioned on a users' skin. In an embodiment, the applicator-skin interface 250 comprises a plurality of active electrodes 206 arranged in an array. A return electrode 204 may be arranged on one side or two opposite sides of the array of active electrodes 206. Using the applicator-skin interface 250, multiple lesions 210 may be created by pulsing an RF source 208 comprised in the shaver-like housing 201. The array of active electrodes 206 may also be replaced by a narrow stripe electrode (not shown) for increased treatment volume applicable to achieve skin firming or tightening.

To better explain the principles used in the embodiments described above, examples of bipolar electrode configurations are described with reference to FIGS. 3A, 3B and 3C.

Figure 3A:
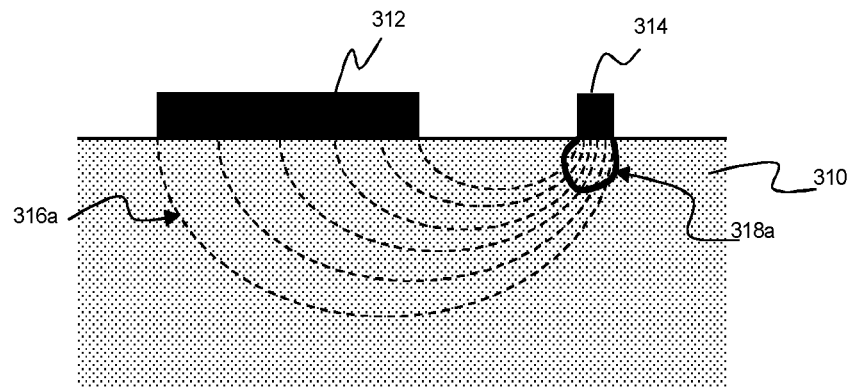
FIG. 3A shows a co-planar configuration of a bipolar electrode according to the prior art on a user's skin tissue.

FIG. 3A shows a co-planar configuration of bipolar electrodes on a user's skin tissue 310 as known from the prior art. A return electrode 312 and an active electrode 314 are placed on a user's skin 310. An RF voltage is applied across the user's skin by means of an RF source (not shown). Upon RF energy delivery, skin tissue regions with the highest spatial density of RF field lines increase in temperature due to RF heating and receive sufficient thermal dosage to cause a thermal lesion. In this case, since the active electrode 314 has a skin contact surface with a maximum dimension in the range from 100 µm to 500 µm, and since the surface area of the planar skin contact surface of the return electrode 312 is at least 5 times larger than the surface area of the skin contact surface of the active electrode, thermolysis mainly occurs immediately below the active electrode 314, where the highest density of the RF field lines 316a is present. This results in a thermal lesion 318a close to and immediately below the active electrode 314. Such a controlled local lesion formation immediately below the active electrode is particularly achieved when the electrode tip of the active electrode making contact with the user's skin has a diameter between 100 and 500 micrometer, while a surface area of the skin contact surface of the return electrode 312 is at least 5 times larger than the surface area of the skin contact surface of the active electrode.

The inventors have found that, by temporarily and non-destructively deforming the skin tissue 310, the radio frequency field between the two electrodes 312 and 314 can be modified, wherein at least one return electrode 312 is positioned on an undeformed portion of the skin tissue region and at least one active electrode 314 on a deformed portion of the skin tissue region. The spatial density of the radio frequency field lines 316 determines the heat distribution generated by the RF energy and thus the tissue temperature distribution and the boundary 318 of the tissue region that undergoes thermolysis.

Figure 3B:
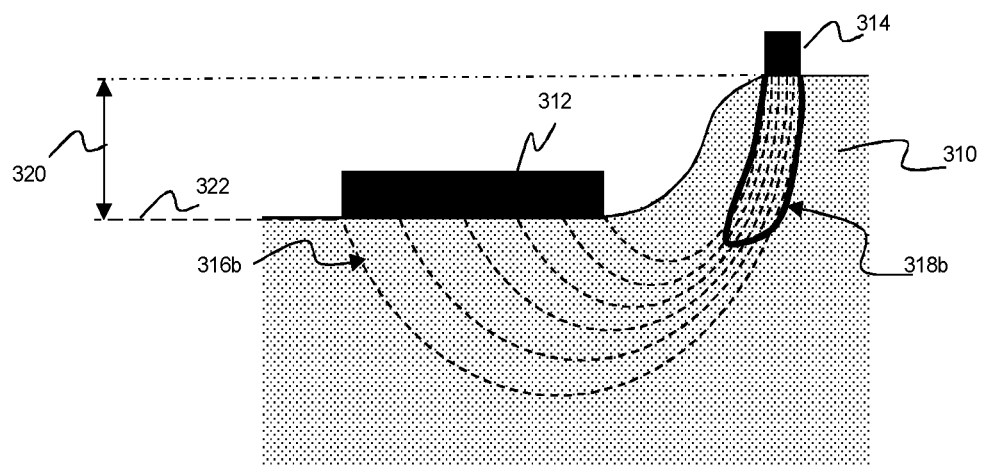
FIG. 3B shows an electrode configuration according to the invention, where an active electrode is positioned on a deformed region of a user's skin tissue, in particular on a skin protrusion.

FIG. 3B shows an electrode configuration, modified as compared to the electrode configuration of FIG. 3A, wherein the active electrode 314 is positioned on top of a deformed region of the skin 310, in particular on top of a skin protrusion. In this case, the RF field lines 318b are modified such that the created thermal lesion 318b is relatively deep and narrow relative to the lesion generated by the co-planar electrodes according to the prior art shown in FIG. 3A. FIG. 3B better explains the principles used in the embodiment of the applicator-skin interface 150A for deep treatment of the skin shown in FIG. 1B. It is noted that the return electrode 312 has a planar skin contact surface, and the planar skin contact surface of the return electrode extends in a main plane 322. The planar skin contact surface of the return electrode 312 is at least 5 times larger than the skin contact surface of the active electrode 314. The skin contact surface of the active electrode 314 has a diameter in the range from 100 µm to 500 µm. The skin contact surface of the active electrode 314 is arranged in a position at a distance 320 from the main plane 322, wherein the distance 320 is measured in a direction perpendicular to the main plane 322. It is noted that this configuration of the return electrode 312 and the active electrode 314 results in a skin deformation such that there is a difference between a skin surface level underneath the active electrode 314 and a skin surface level underneath the return electrode 312. In particular, the skin surface level underneath the active electrode 314 is above the skin surface level underneath the return electrode 312.

Figure 3C:
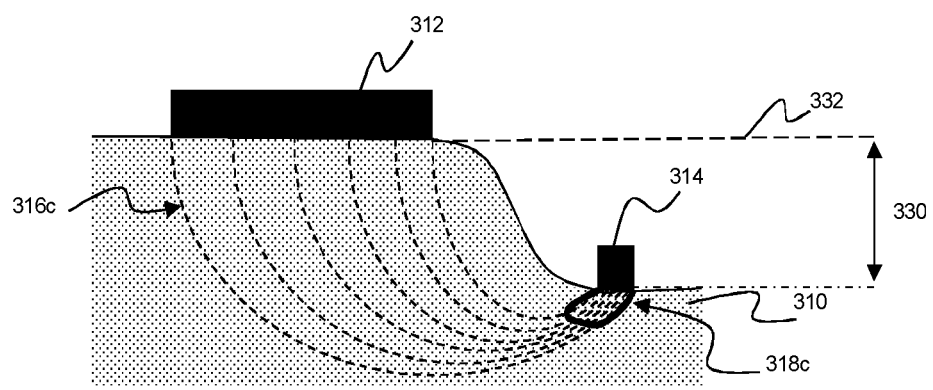
FIG. 3C shows an electrode configuration according to the invention, where an active electrode is positioned on a deformed region of a user's skin, in particular on a skin indentation.

FIG. 3C shows an electrode configuration, modified as compared to the electrode configuration of FIG. 3A, wherein the active electrode 314 is positioned on a deformed region of the skin, in particular in an indentation of the skin. In this case, the RF field lines 318c are modified such that the created thermal lesion 318c is more superficial and shallow as compared to the lesion generated by the co-planar electrodes according to the prior art shown in FIG. 3A. FIG. 3C better explains the principles used in the embodiment of the applicator-skin interface 150B for superficial treatment of the skin shown in FIG. 1C. It is noted that the return electrode 312 has a planar skin contact surface, and the planar skin contact surface of the return electrode 312 extends in a main plane 332. The planar skin contact surface of the return electrode 312 is at least 5 times larger than the skin contact surface of the active electrode 314. The skin contact surface of the active electrode 314 has a diameter in the range from 100 µm to 500 µm. The skin contact surface of the active electrode 314 is arranged in a position at a distance 330 from the main plane 332, wherein the distance 330 is measured in a direction perpendicular to the main plane 332. It is noted that this configuration of the return electrode 312 and the active electrode 314 results in a skin deformation such that there is a difference between the skin surface level underneath the active electrode 314 and the skin surface level underneath the return electrode 312. In particular, the skin surface level underneath the active electrode 314 is below the skin surface level underneath the return electrode 312.

In the above mentioned embodiments according to the invention, as shown in FIG. 3B and FIG. 3C, a substantial modification of the profile of the lesion 318a formed by the prior art electrode configuration of FIG. 3A is particularly achieved when the distance 320 and the distance 330, respectively, are larger than 0.5 mm. Accordingly, the invention does not apply to co-planar electrode configurations as shown in FIG. 3A wherein, as a result of manufacturing tolerances, a small deviation from the co-planarity of the electrodes is present. In other words, in an electrode configuration according to the invention the distance between the skin contact surface of the active electrode and the main plane is substantial, for example larger than 20% of the diameter of the skin contact surface of the active electrode or, more preferably, larger than 50% of the diameter of the skin contact surface of the active electrode.

Computer simulations have provided further insight that changing the shape of the skin and placing the electrodes at different skin surface levels may directly influence lesion geometry. The simulations showed lesion depths of 100 micrometer (µm), 95 µm and 115 µm for the co-planar, skin indentation, and skin protrusion configurations, respectively, (see table 1) for a 50 millisecond (ms) RF pulse duration. Indeed, the simulations showed that skin deformation may result in control of the lesion profile, particularly depth and aspect ratio. Relative to the reference co-planar configuration, for the skin protrusion configuration 15% increase in depth and aspect ratio and for the skin indentation configuration 5% decrease in depth and aspect ratio may be achieved. Additional simulations using 20 ms and 200 ms pulse durations showed similar trends of increased lesion depths with skin protrusion and decreased lesion depths for skin indentation.

TABLE 1 lesion depths and diameters (depth/diameter) for the different electrode configurations shown in FIGS. 3A-C.

| Configuration | 20 ms | 50 ms | 200 ms |
|---|---|---|---|
| Co-planar (A) | 75 µm/205 µm | 100 µm/210 µm | 120 µm/250 µm |

TABLE 1-continued lesion depths and diameters (depth/diameter) for the different electrode configurations shown in FIGS. 3A-C.

| | | | |
|---|---|---|---|
| Skin Indentation (B) | 70 µm/200 µm | 95 µm/205 µm | 80 µm/220 µm |
| Skin Protrusion (C) | 85 µm/215 µm | 115 µm/220 µm | 145 µm/270 µm |

Figure 4:
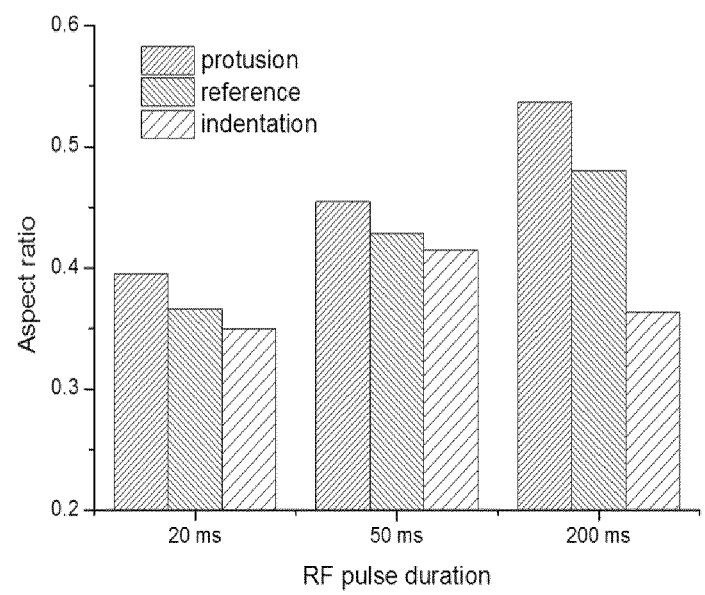
FIG. 4 shows calculation results of an aspect ratio of lesions created by means of different electrode configurations according to the invention for different RF pulse durations.

In the embodiments described above, the aspect ratio between lesion depth and diameter may be controlled. FIG. 4 shows simulation results showing the aspect ratio of the lesions created using different configurations at different RF pulse durations. For three exemplary RF pulse durations of 20 ms, 50 ms and 200 ms, a skin protrusion configuration results in a higher aspect ratio, and a skin indentation configuration results in a lower aspect ratio, relative to a co-planar reference configuration. Moreover, increased relative difference in aspect ratio is observed for longer RF pulse durations.

Figures 5A, 5B:
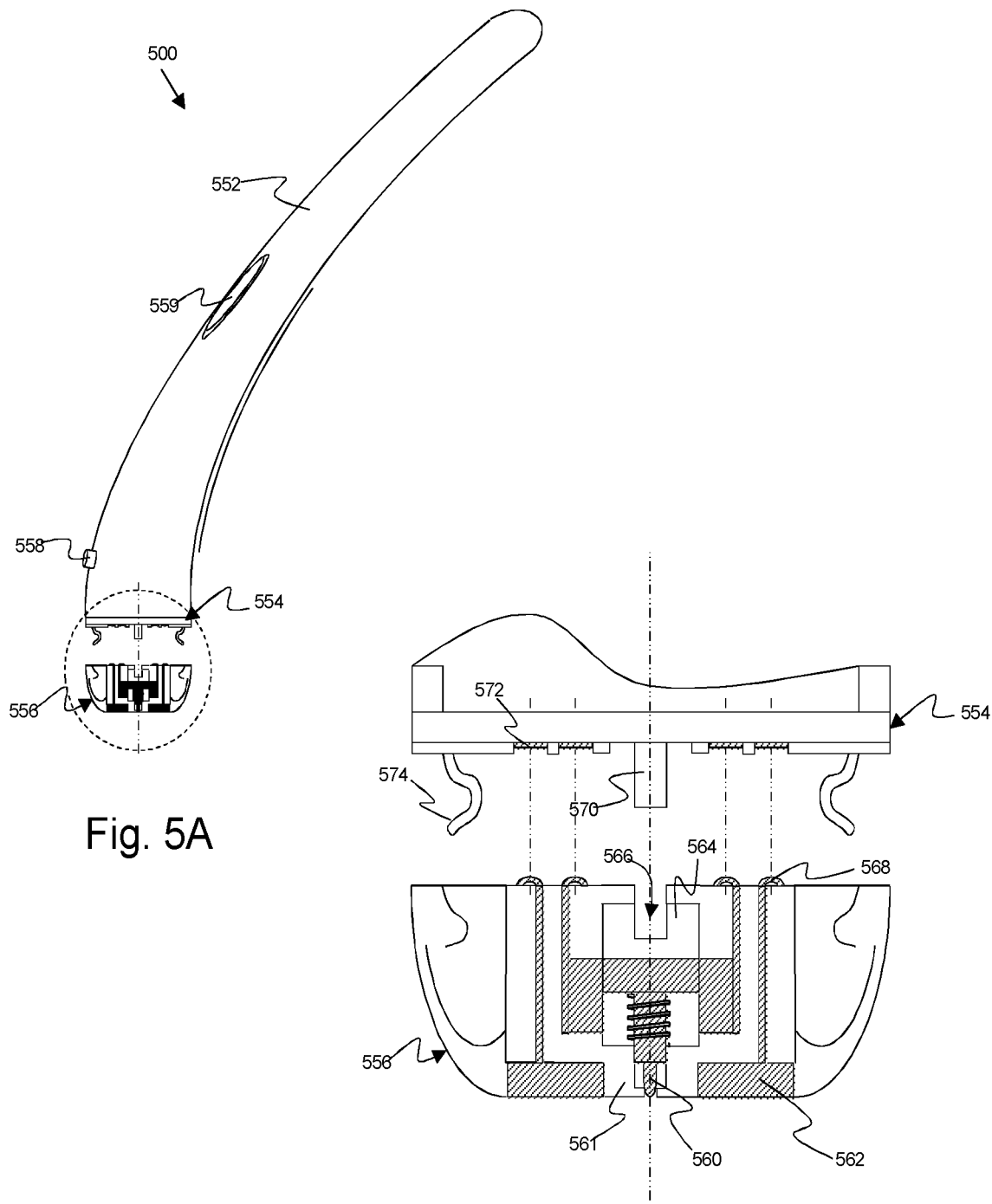
FIG. 5A shows a perspective view of a device for RF skin treatment according to another embodiment of the invention.
FIG. 5B shows a cross-sectional view of an applicator head and an applicator connector of the device of FIG. 5A.

FIG. 5A shows a perspective view of a RF treatment device 500 according to a further embodiment of the invention. This device 500 comprises a handle mount 552, an applicator connector 554, and a detachable applicator head 556. An RF power supply (not shown) and a control circuit are accommodated within the handle mount 552. The RF power supply may be enabled by a power button 559. To control a height of a protrusion of the microelectrode 560, a control button 558 may be provided.

FIG. 5B shows a cross sectional view of the applicator head 556 and the applicator connector 554. The applicator connector 554 comprises a protrusion height control tip 570, an electrode connector mount interface 572, and an applicator-mount interlocking mechanism 574. The applicator head 556 comprises a microelectrode 560, a skin-contact element 561, a ring-shaped return electrode 562, a movable spring-loaded shaft 564, a shaft recess 566 for connecting the protrusion height control tip 570, and an electrode connector applicator interface 568. The control button 558 may be mechanically coupled to the protrusion height control tip 570. The control button 558 may also be electronically coupled to an electromechanical actuator (not shown) for a more precise adjustment of the protrusion height of the microelectrode 560.

Figure 6:
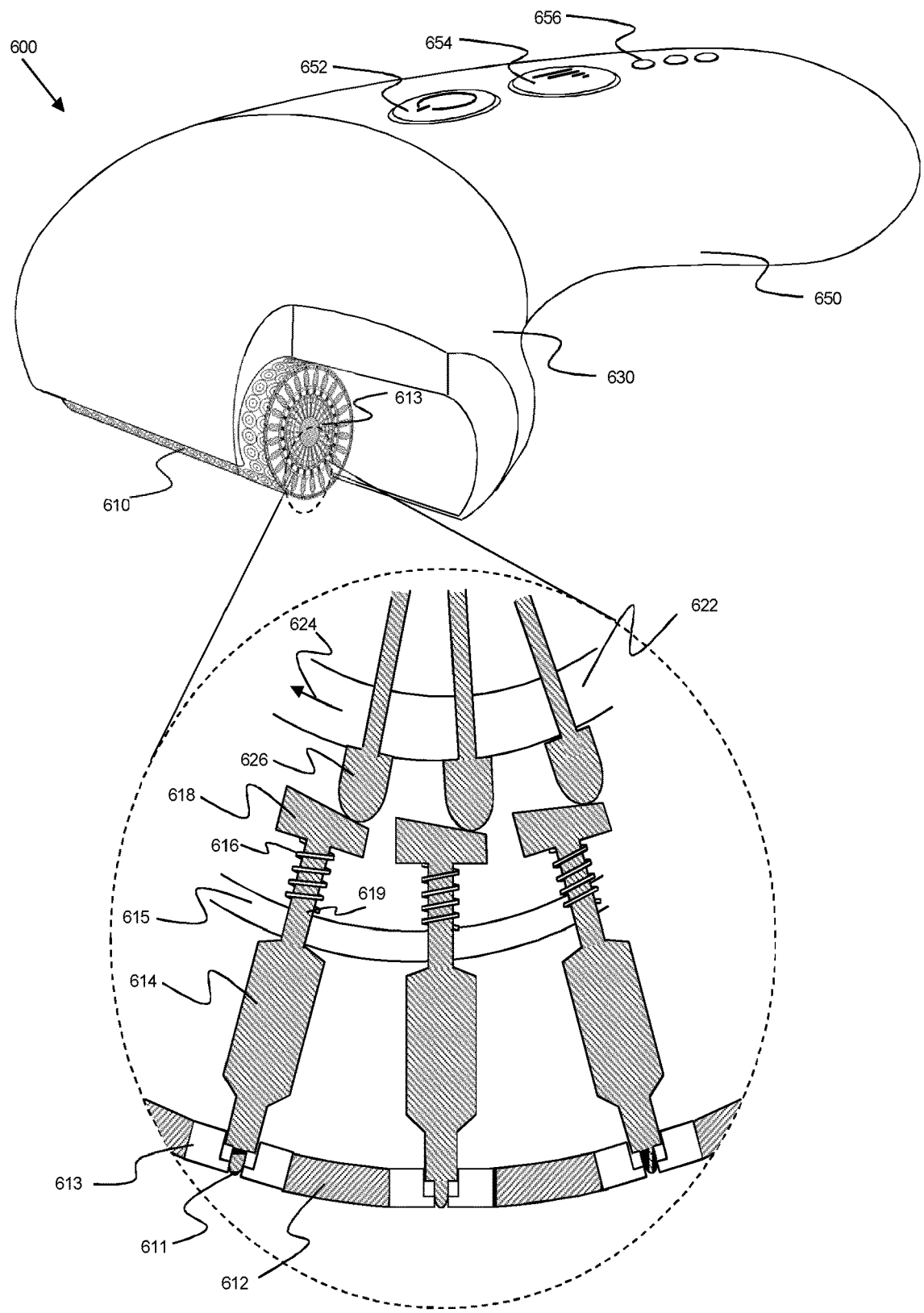
FIG. 6 shows a perspective view and a cross-sectional view of an RF treatment device comprising a rotatable assembly according to another embodiment of the invention.

FIG. 6 shows a perspective view and a cross sectional view of an RF treatment device 600 comprising a rotatable assembly according to a further embodiment of the invention. The device 600 comprises an applicator mount assembly 630, a rotatable assembly herein also referred to as a rolling applicator head 610 and a handle mount 650. The rolling applicator head 610 comprises concentric ring-shaped return electrodes 612 and an array of active electrodes 611 arranged in a cylindrical skin-contact element 613. The skin-contact element 601 comprises multiple openings, wherein each active electrode 611 is movably arranged in a corresponding opening. A respective skin contact element 613 is provided between each active electrode 611 and the corresponding return electrode 612. The tip of the active electrode 611 may be a rounded cylindrical or a rounded conical tip, or another rounded complex shaped tip that increases the contact area when pressed onto an elastic material, e.g. skin. Each active electrode 611 is connected to a holding body 614. The holding body 614 is connected to an active electrode body 619 which is connected to a diagonally tapered end 618. The active electrode body 619 is held by a spring 616 which is anchored to the rolling applicator head 610 through a fixed disc 615, such that at the maximum length of the spring 616 the active electrode tip 611 is at its innermost position and, in use, the active electrode 611 is in contact with skin with a minimal contact area. The diagonally tapered ends 618 of the active electrode bodies 619 are in contact with a rotating shaft 622 through respective round-tipped spokes 626. When the rotating shaft 622 is rotated in a certain direction 624, the spokes 626 rotate and slide on the surfaces of the diagonally tapered ends 618 of the active electrode bodies, causing the active electrode bodies 619 and the active electrode 611 to move radially outward, and, in use, resulting in a larger contact area between each active electrode 611 and the skin. The rotating shaft may be connected to a rotating motor for electrical control.

The handle mount 650 may comprise control interface buttons, e.g. a power button 652, a treatment coverage settings button 654, and a treatment coverage settings light indicator 656, a device housing assembly, a power supply, e.g. a rechargeable battery, a RF source and control circuitry (not shown in FIG. 6).

The applicator mount assembly 630 holds the rolling applicator head 610 at its axis of rotation, allowing rotation of the applicator head 610. The applicator mount assembly 630 may also comprise rotating electrical connectors, e.g. slip rings, that electrically connect the electrical components, e.g. electrodes and rotating motor, provided inside the rolling applicator head 610 to the electrical components, e.g. RF source, power sources and electronic signals provided inside the handle mount 650.

To better explain the principles used in the exemplary devices 500 and 600 described above, examples of bipolar electrodes in contact with skin 710 are described with reference to FIGS. 7A and 7B. Furthermore, histological data of deformation experiments on ex-vivo human skin are subsequently provided with reference to FIGS. 8A, 8B, 8C and 8D.

Figure 7A:
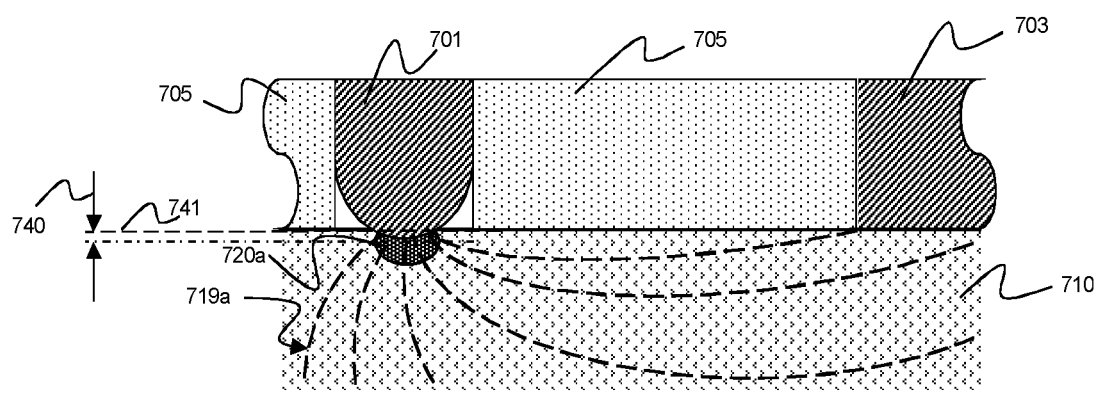
FIG. 7A shows an electrode configuration according to the invention, wherein an active electrode is positioned so as to apply a minimal pressure to a user's skin in order to form a skin indentation.

FIG. 7A shows a cross sectional view of an active electrode 701 and a return electrode 703 placed on the user's skin 710. An RF voltage is applied across the user's skin 710 by means of an RF source (not shown) and the active electrode 701 applies a minimal skin deformation. RF field lines 719a result in the creation of a lesion 720a. In this case, a certain thermal dosage results in a relatively narrow lesion. It is noted that the return electrode 703 has a planar skin contact surface, and the planar skin contact surface of the return electrode defines a main plane 741. The surface area of the planar skin contact surface of the return electrode 703 is at least five times larger than the surface area of the skin contact surface of the active electrode 701. The skin contact surface of the active electrode is at a distance 740 from the main plane 741, the distance 740 being measured in a perpendicular direction from the main plane 741. It is noted that this configuration of return electrode 703 and active electrode 701 results in a skin deformation such that there is a difference between the skin surface level underneath the active electrode 701 and the skin surface level underneath the return electrode 703. It is noted that in case of a curved skin contact surface of the active electrode, the distance from the distance 740 may be measured from an extremity of the curved surface to the main plane 741.

Figure 7B:
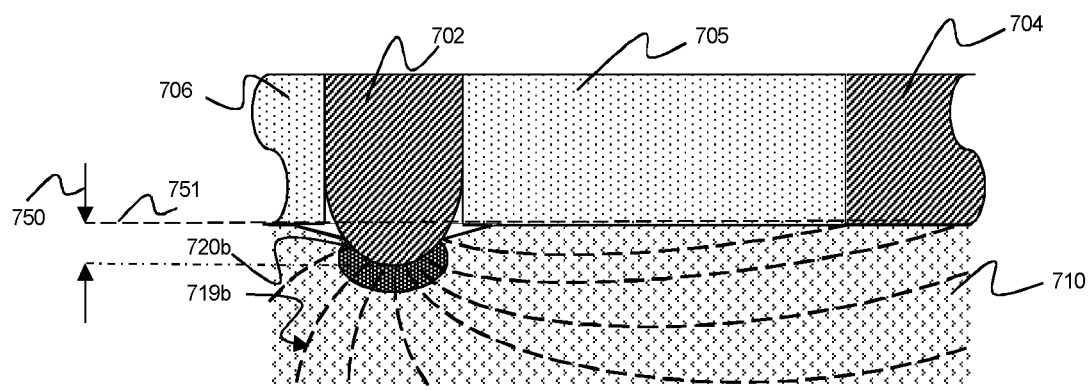
FIG. 7B shows an electrode configuration according to the invention, wherein an active electrode is positioned so as to apply pressure to a user's skin in order to form a skin indentation.

FIG. 7B shows a cross sectional view of a skin indentation configuration where an active electrode 702 and a return electrode 704 are placed on a user's skin 710; an RF voltage is applied across the user's skin by means of an RF source (not shown). By placing the RF treatment devices 500, 600 on the user's skin, a pressure is applied to the user's skin 710 by the devices 500, 600. Since the active electrode 702 protrudes/extends from the skin contact element 705, the user's skin 710 is locally deformed and the electrode-skin contact area is increased. The increased contact area between the active electrode 702 and the user's skin 710 results in a modification of the RF field lines 719b, resulting in the creation of a wider lesion 720b. Uncontrolled local skin deformations around the active electrode are minimized by a skin contact element 705. The skin contact element 705 may be made from an electrically non-conducting material placed around the active electrode 702 and between the active electrode 702 and the return electrode 704 to keep a surface of the skin 710 substantially co-planar with the return electrode 704. It is noted that the return electrode 704 has a planar skin contact surface, and the planar skin contact surface of the return electrode defines a main plane 751. The surface area of the planar skin contact surface of the return electrode 704 is at least five time larger than the skin contact surface of the active electrode 702. The skin contact surface of the active electrode is at a distance 750 from the main plane 751, the distance 750 being measured in a perpendicular direction from the main plane 751. It is noted that this configuration of the return electrode 704 and active electrode 702 results in a skin deformation such that there is a difference between the skin surface level underneath the active electrode 702 and the skin surface level underneath the return electrode 704.

Figure 8A:
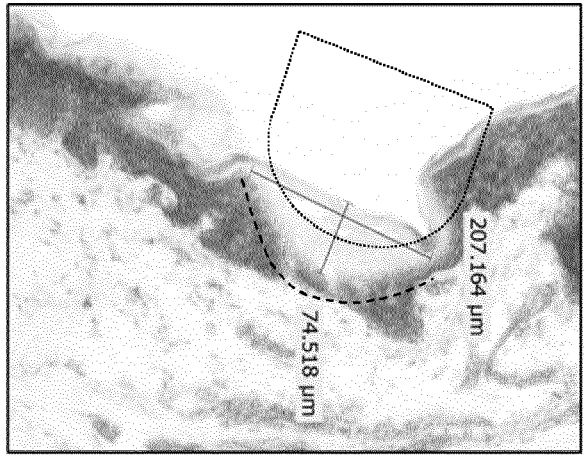
FIG. 8A shows histological data of minimal deformation experiments by means of an active electrode having a diameter of 200 μm and using an RF voltage of 40 rms Volts.
Figure 8B:
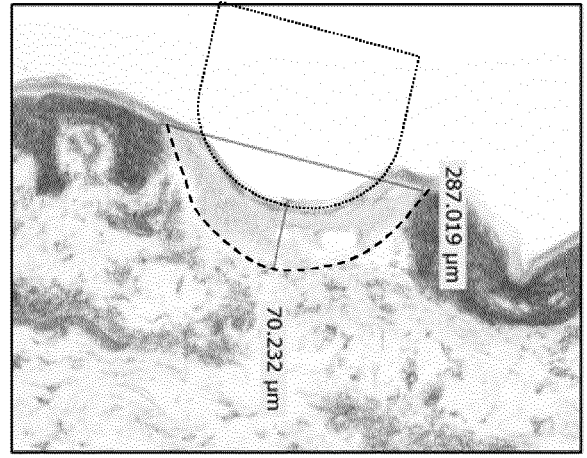
FIG. 8B shows histological data of deep deformation experiments by means of an active electrode having a diameter of 200 μm and using an RF voltage of 40 rms Volts.
Figure 8C:
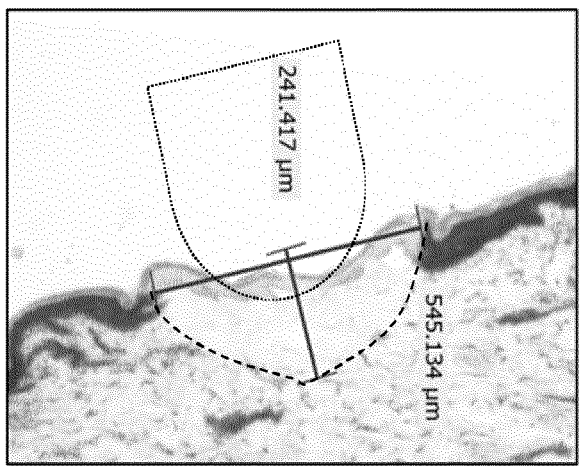
FIG. 8C shows histological data of minimal deformation experiments by means of an active electrode having a diameter of 400 μm and using an RF voltage of 50 rms Volts.
Figure 8D:
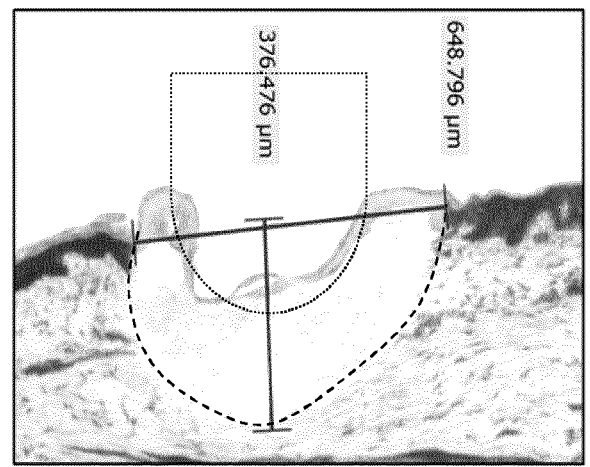
FIG. 8D shows histological data of deep deformation experiments by means of an active electrode having a diameter of 400 μm and using an RF voltage of 50 rms Volts.

FIG. 8A, FIG. 8B, FIG. 8C and FIG. 8D show histological data obtained from experiments performed on ex-vivo human skin, wherein different lesion widths are created with different deformations of an active electrode on the skin. In all cases, a concentric ring-shaped return electrode having an inside diameter of 2 millimeter (mm) and outside diameter of 10 mm was used. FIG. 8A and FIG. 8B show results of experiments performed with an active electrode with a diameter of 200 μm and using an RF voltage of 40 rms Volts. FIG. 8C and FIG. 8D show results of experiments performed with an active electrode with a diameter of 400 μm and using an RF voltage of 50 rms Volts. In FIG. 8A, a minimal deformation resulted in a lesion width of 207 μm. In FIG. 8B, a deeper deformation of the skin by the active electrode resulted in a lesion width of 287 μm, i.e. approximately 40% increase in width corresponding to approximately a two-fold increase in lesion area. In FIG. 8C, using the active electrode with a diameter of 400 μm, an increase of the deformation increased the lesion width from 545 μm to 650 μm, corresponding to a 40% increase of the lesion area. These results exemplify the impact of changing the deformation depth on the area of the created lesion and hence on the RF treatment coverage.

It is noted that, in general, the invention features devices and methods for coupling radio frequency energy to skin, e.g., when delivering radio frequency energy to target tissue to create non-ablative lesions for fractional radio frequency skin treatment. The devices and tools control the delivery of radio frequency energy to the target tissue, such that the depth and width of the created lesion can be controlled. By providing a bipolar electrode configuration in a non-coplanar configuration relative to the skin surface and modifying the skin tissue topology, e.g. by creating a skin protrusion or indentation, the radio frequency field lines may be modified and this may result in control of the lesion profile. The present invention may provide a simple and low-cost solution enabling the control of RF thermal lesion depth and width. This may be beneficial for providing flexibility to RF skin treatment devices used for different depth- and width-dependent skin treatment purposes, e.g. shallow lesions for pigmentation problems and deep lesions for wrinkle reduction.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A device for radio frequency (RF) skin treatment of skin of a user, the device comprising:
    an applicator skin interface comprising an active electrode, a return electrode and a dome-shaped insulating element comprising a protrusion with a single opening at the top of an outer surface with the active electrode arranged therein, the return electrode arranged adjacent to the protrusion surrounding the active electrode and having a planar skin contact surface extending in a main plane, a tip of the active electrode being centrally arranged in an indentation of the skin interface formed by the dome-shaped protrusion, such that in use, the tip of the active electrode is in electrical contact with an upper region of a protruding skin region and the return electrode is in electrical contact with a flat undeformed portion of the surface of the skin;
    wherein the active electrode has a skin contact surface with a maximum dimension in a range from 100 μm to 500 μm to effect a controlled lesion formation immediately below the active electrode, wherein the maximum dimension corresponds to a maximum diameter between two points on an outer circumference of the skin contact surface;
    wherein an inside diameter of the return electrode and the outside diameter of the dome-shaped insulating element are co-planar at their respective distal ends;
    an RF generator arranged to supply, during use, RF energy to the skin via the skin return electrode and the active electrode;
    wherein the skin contact surface of the active electrode is arranged in a position seen in a direction perpendicular to the main plane at a distance larger than 0.5 mm from the main plane; and
    wherein the device controls the delivery of radio frequency energy to target tissue such that the depth and width of created lesions can be controlled by providing a bi-polar electrode configuration in a non-coplanar configuration relative to a skin surface and modifies radio frequency field liens to control a lesion profile, thereby enabling the control of RF thermal lesion depth and width.

2. The device according to claim 1, wherein the planar skin contact surface of the return electrode is annular.

3. The device according to claim 2, wherein the planar skin contact surface has an inside diameter between 1 and 4 mm and a radial width between 1 and 5 mm.

4. The device according to claim 2, wherein the active electrode is arranged on a center line of the planar skin contact surface.

5. The device according to claim 1, wherein an outer surface of the device comprises an indentation, wherein the active electrode is arranged in the indentation, and wherein the return electrode is arranged adjacent to the indentation.

6. The device according to claim 5, wherein the indentation is dome-shaped.

7. The device according to claim 1, wherein the return electrode is arranged adjacent to the indentation and surrounds the active electrode.

8. The device according to claim 1, wherein the return electrode is in electrical contact with a flat undeformed portion of the skin.

9. The device according to claim 1, wherein a concentration of electric field lines in the skin in a region immediately below the active electrode results in the creation of a local lesion below the active electrode.

10. A device for radio frequency (RF) skin treatment of skin of a user, the device comprising:
an applicator skin interface comprising a plurality of active electrodes, a return electrode and a dome-shaped insulating element comprising a protrusion with a single opening a the top of an outer surface with the plurality of active electrodes arranged therein, the dome-shaped insulating element comprising an opening having a main axis of extension, wherein the plurality of active electrodes are arranged in said opening and arranged at different positions along a main axis of extension, the plurality of active electrodes being arranged in an array having a skin contact surface with a maximum dimension in a range from 100 µm to 500 µm, wherein said maximum dimension corresponds to a maximum diameter between two points on an outer circumference of the skin contact surface;
wherein a combination of the plurality of active electrodes having a skin contact surface with a maximum dimension in a range from 100 µm to 500 µm, the surface area of the planar skin contact surface of the return electrode being at least 5 times larger than a surface area of the skin contact surface of the plurality of active electrodes and the plurality of active electrodes being positioned to be non-coplanar with the return electrode results in a deep and local thermal lesion being generated proximal to and immediately below the plurality of active electrodes;
a return electrode having a planar skin contact surface, the planar skin contact surface of the return electrode extending in a main plane; and
an RF generator arranged to supply, during use, RF energy to the skin via the return electrode and the plurality of active electrodes;
wherein a tip of the plurality of active electrodes is centrally arranged in the device in electrical contact with a locally deformed portion of the surface of the skin; and
wherein at least an inner surface of a central portion of the device is made of an electrically insulating material,
wherein an inside diameter of the return electrode and the outside diameter of the dome-shaped insulating element are co-planar at their respective distal ends, and
wherein a placement and an arrangement of the plurality of active electrodes, the return electrode and the dome-shaped insulating element controls a local deformation of the skin of the user thereby controlling a lesion profile directed to the dimension and shape of lesions created in the skin of the user independent of the RF frequency, RF pulse duration and tissue impedance.

11. The device according to claim 10, wherein the return electrode is in electrical contact with a flat undeformed portion of the skin.

12. The device according to claim 10, wherein the return electrode is arranged on one side of the array of active electrodes.

13. The device according to claim 10, wherein the return electrode is arranged on two sides of the array of active electrodes.

14. The device according to claim 10, wherein the return electrode surrounds a active electrode.

15. A device for radio frequency (RF) skin treatment of skin of a user, the device comprising:
an applicator skin interface comprising a plurality of active electrodes, a return electrode and a dome-shaped insulating element comprising a protrusion with a single opening at the top of an outer surface with the plurality of active electrodes arranged therein, the dome shaped insulating element comprising an opening having a main axis of extension, wherein the plurality of active electrodes are arranged in said opening and arranged at different positions along a main axis of extension, the plurality of active electrodes being arranged in an array having a skin contact surface with a maximum dimension in a range from 100 µm to 500 µm, wherein said maximum dimension corresponds to a maximum diameter between two points on an outer circumference of the skin contact surface;
wherein a combination of the plurality of active electrodes having a skin contact surface with a maximum dimension in a range from 100 µm to 500 µm, the surface area of the planar skin contact surface of the return electrode being at least 5 times larger than a surface area of the skin contact surface of the plurality of active electrodes and the plurality of active electrodes being positioned to be non-coplanar with the return electrode results in a local thermal lesion being generated proximal to and immediately below the plurality of active electrodes;
a return electrode having a planar skin contact surface, the planar skin contact surface of the return electrode extending in a main plane; and
an RF generator arranged to supply, during use, RF energy to the skin via the return electrode and the plurality of active electrodes;
wherein a tip of the plurality of active electrodes is centrally arranged in the device in electrical contact with a locally deformed portion of the surface of the skin;
wherein at least an inner surface of a central portion of the device is made of an electrically insulating material; and
wherein a surface area of the planar skin contact surface of the return electrode is at least 5 times larger than a surface area of the skin contact surface of the active electrode;
wherein the skin contact surface of the active electrode is arranged or arrangeable in a position at a distance from the main plane, seen in a direction perpendicular to the main plane,
wherein an inside diameter of the return electrode and the outside diameter of the dome-shaped insulating element are co-planar at their respective distal ends, and
wherein a placement and an arrangement of the plurality of active electrodes, the return electrode and the dome-shaped insulating element controls a local deformation of the skin of the user thereby controlling a lesion profile directed to the dimension and shape lesions created in the skin of the user independent of the RF frequency, RF pulse duration and tissue impedance.

16. The device according to claim 15, wherein the return electrode is arranged on one side of the array of active electrodes.

17. The device according to claim 15, wherein the return electrode is arranged on two sides of the array of active electrodes.

18. The device according to claim 15, wherein the return electrode surrounds the active electrode.

* * * * *